(12) United States Patent
Trotter et al.

(10) Patent No.: US 8,808,754 B2
(45) Date of Patent: Aug. 19, 2014

(54) METHODS FOR THE TREATMENT OF WOUNDS

(75) Inventors: Patrick J. Trotter, Leeds (GB); Frank R. Cichocki, Jr., Easton, PA (US)

(73) Assignee: Systagenix Wound Management (US), Inc., Wilmington, DE (US)

( * ) Notice: Subject to any disclaimer, the term of this patent is extended or adjusted under 35 U.S.C. 154(b) by 2036 days.

(21) Appl. No.: 11/477,307

(22) Filed: Jun. 29, 2006

(65) Prior Publication Data

US 2008/0003299 A1     Jan. 3, 2008

(51) Int. Cl.
*A61K 33/00* (2006.01)
*A61P 17/02* (2006.01)
*A61M 35/00* (2006.01)
*A61H 33/14* (2006.01)

(52) U.S. Cl.
CPC ............... *A61M 35/00* (2013.01); *A61H 33/14* (2013.01)
USPC ............ 424/613; 604/23; 604/24; 604/93.01; 604/264

(58) Field of Classification Search
None
See application file for complete search history.

(56) References Cited

U.S. PATENT DOCUMENTS

| | | | |
|---|---|---|---|
| 4,224,941 A | 9/1980 | Stivala | |
| 4,624,656 A | 11/1986 | Clark et al. | |
| 5,662,625 A | 9/1997 | Westwood | |
| 5,810,795 A | 9/1998 | Westwood | |
| 6,139,876 A | 10/2000 | Kolta | |
| 6,179,804 B1 | 1/2001 | Statterfield | |
| 6,626,885 B2 | 9/2003 | Massengale | |
| 2002/0160053 A1 | 10/2002 | Yahagi et al. | |
| 2003/0021751 A1* | 1/2003 | Eckert | 424/9.52 |
| 2005/0125035 A1 | 6/2005 | Chicocki, Jr. | |

FOREIGN PATENT DOCUMENTS

| | | | |
|---|---|---|---|
| FR | 2656218 A | | 6/1991 |
| GB | 2409412 A | | 6/2005 |
| WO | WO 9741816 A | | 11/1997 |
| WO | WO 9853778 A | | 12/1998 |
| WO | WO 0038767 A | | 7/2000 |
| WO | WO 2005055836 A2 * | | 6/2005 |

OTHER PUBLICATIONS

East, file Derwent, Acc. No. 2004-802881 (RU 2237473 C1 (2004)), Abstract.*
Pubmed online, file Medline, PMID 10984756 (Thomas et al., Wound management in postacute care, Clin. Geriatr. Med. (2000), vol. 16, No. 4, pp. 783-804), Abstract.*
Pubmed online, file Medline, PMID 14617261(Simonsen et al., Clin. Physiol. Funct. Imaging (2003), vol. 23, No. 6, pp. 320-323), Abstract.*
Ward et al., Measurement of localized tissue water-clinical application of bioimpedence spectroscopy in wound management, Journal of Physics: Conference Series 434 (2013), pp. 1-4.*
Broughton et al., Wounds and Scars, Selected Readings in Plastic Surgery (2005), vol. 10, No. 7, Part 1, pp. 1-54.*

* cited by examiner

*Primary Examiner* — Abigail Fisher
*Assistant Examiner* — Frank Choi

(57) ABSTRACT

A method of treatment of a wound, said method comprising the step of injecting an effective amount of an oxygen-containing fluid into said wound at a location below a surface of said wound, said step of injecting being carried out through a conduit having one or more outlets for said fluid, wherein substantially all of said outlets are positioned below the surface of the wound during said step of injecting. Injection of oxygen directly into the wound tissue below the wound surface provides enhanced wound healing.

17 Claims, 3 Drawing Sheets

METHODS FOR THE TREATMENT OF WOUNDS

FIELD OF THE INVENTION

The present invention relates to methods for treating wounds and lesions on a patient's body by introducing an oxygen-containing fluid into a tissue beneath the surface of the wound or lesion.

BACKGROUND OF THE INVENTION

The effect of oxygen on wound healing has been extensively studied. Wound healing is dependent upon several processes including proliferation of fibroblasts, collagen synthesis, angiogenesis and re-epithelialization. Many skin sores, ulcers, wounds and burns do not heal properly because there is a severe depletion of oxygen reaching these affected areas due to deterioration of the associated blood microcirculation. Tissue oxygen levels have previously been measured in non-healing wounds to be (5-20 mmHg) as compared to control tissue values of 30-50 mmHg.

Hitherto, many of these wound healing disorders have been treated by various methods of administration of oxygen gas, known as, either through inhalation of the gas in hyperbaric oxygen therapy, or by topical treatment with the gas.

Treatments based on inhalation of oxygen, while considered effective, are complex and entail a risk from the potential harmful effects of prolonged hypoxia.

Numerous wound treatment devices are known that administer oxygen gas topically to wound surfaces. Examples can be found in GB-A-2409412, WO-A-9853778, U.S. Pat. No. 6,179,804, U.S. Pat. No. 4,624,656, U.S. Pat. No. 4,224,941, U.S. Pat. No. 5,662,625, U.S. Pat. No. 5,810,795, FR-A-2656218 and WO-A-9741816. These devices generally comprise an impermeable sheet having a peripheral region for attachment in gas-tight fashion around the wound, for example with adhesive, to form an enclosed chamber over the wound. The devices further comprise a gas inlet for introducing oxygen gas into the chamber above the wound, and optionally an outlet for removal of gas from the chamber. The devices can be operated with a static charge of gaseous oxygen, or with a continuous flow of gaseous oxygen over the wound. It will be appreciated that such devices are relatively bulky and prone to leakage, and can interfere with dressing changes and removal of wound exudates.

U.S. Pat. No. 6,139,876 describes a gelatin with increased oxygen content for use as a topical wound dressing. The gelatin comprises a gelling agent, a solvent, and microbubbles of oxygen in a substantially even distribution with a partial pressure exceeding normal atmospheric pressure, wherein the surface tension of the gelatin is sufficiently high to retain at least a portion of the overpressure of the oxygen throughout a predetermined period of time after having been exposed to an atmospheric environment.

US20020160053 describes an aqueous solution for promoting the growth of tissue cells at wound sites. This solution comprises water containing at least 1 to 500 ppm of active oxygen and 10 to 10000 ppm of halogen ions. The solution is produced by electrolysis of aqueous halide solutions. The active oxygen can include singlet oxygen formed by excitation of triplet oxygen, superoxide formed by reduction of oxygen by a single electron, and hydroxy radical, as well as hypochlorous ions, organic peroxy radicals (ROO.), alkoxy radicals (RO.), and organic hydroperoxides (ROOH). However, the physiological effects of these reactive oxygen species differ from the effect of oxygen gas, and indeed the reactive oxygen species can be deleterious to wound healing.

U.S. Pat. No. 2,005,0125035 describes an active suture having an internal passageway for post-surgical delivery of active fluids. The active fluids may comprise a wide range of medicaments, including oxygen-rich liquids to assist wound healing.

SUMMARY OF THE INVENTION

In a first aspect, the present invention provides a method of treatment of a wound, said method comprising the step of injecting an effective amount of an oxygen-containing fluid into said wound at a location below a surface of said wound, said step of injecting being carried out through a conduit having one or more outlets for said fluid, wherein substantially all of said outlets are positioned below the surface of the wound during said step of injecting.

In a second aspect, the present invention provides a method of treatment of a wound, said method comprising the step of injecting an effective amount of an oxygen-containing fluid selectively and directly into a layer of wound tissue located below a surface layer of said wound.

In a third aspect, the present invention provides a method of treatment of a wound, said method comprising the step of injecting an effective amount of an oxygen-containing fluid into said wound at a predetermined depth below a surface of said wound, preferably substantially without injecting said oxygen-containing fluid into healthy tissue surrounding the wound.

In a fourth aspect, the present invention provides a method of treatment of a wound without suturing of said wound, said method comprising the step of injecting an effective amount of an oxygen-containing fluid directly into a granulation tissue layer of said wound below a surface of the wound.

In a further aspect, the present invention provides the use of oxygen for the preparation of an oxygen-containing fluid for use in the treatment of wounds by a method according to any aspect of the present invention.

DETAILED DESCRIPTION OF THE INVENTION

Figure 1:
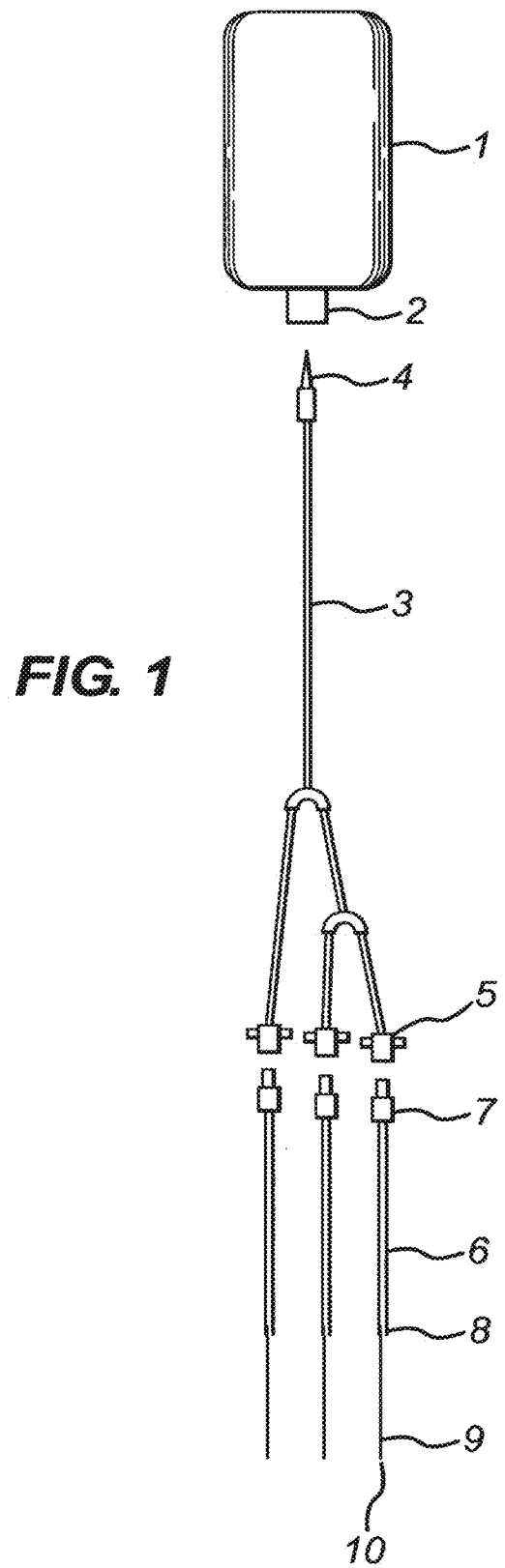
FIG. 1 shows a schematic expanded view of an apparatus for use in a method according to the present invention.

It has been found that water containing oxygen dissolved under pressure can be injected directly into wound tissue at a rate sufficient to have a positive effect on wound healing, without forming a gas bolus in the wound tissue. It has further been found that injection of oxygen-containing fluid into the wound tissue in this way is even more beneficial to wound healing than topical application of the oxygen-containing fluid to the wound. In particular, the amount of granulation tissue deposited (as determined both visually and by histological analysis) was significantly greater when oxygen-containing fluid was delivered into the tissue rather than onto the surface of the tissue.

The present invention differs from the use of active sutures to deliver oxygen rich liquids, because the present invention delivers the oxygen rich liquid directly and selectively to the wound tissue below the surface of the wound, without any of the damage to surrounding healthy tissue that is caused by suturing. The present invention delivers the oxygen directly to the granulation tissue layer of the wound, where it is most effective. The present invention is especially useful for the treatment of chronic wounds such as ulcers that are not normally sutured. Furthermore, the apertured sutures of U.S. Pat. No. 2,005,0125035 deliver oxygen rich fluid nonselectively along the length of the suture. It follows also that the apertured sutures cannot be used to deliver an oxygen enriched fluid under pressure to a predetermined tissue layer under the surface of the wound, since the fluid under pressure will leak out of exposed parts of the apertured suture.

The conduit through which the oxygen-containing liquid is normally delivered to the wound tissue may be a microcatheter. The term "microcatheter" refers to any tubular body having a small internal and external diameter, including micro-injection needles, syringes, hollow sutures, and the like. Suitable microcatheters are described, for example, in US-B-6626885.

Preferably, the conduit is flexible. Suitably, the conduit has a substantially cylindrical lumen with one or more outlet apertures in a tip region thereof, but no apertures intermediate the inlet and the tip apertures, whereby all of the fluid injected into the inlet of the catheter flows out near the tip, i.e. below the surface of the wound in use. It will be appreciated that multiple conduits, or a single conduit with multiple outlets, may be used to deliver the oxygen-containing fluid to the wound. In certain embodiments, the conduit is branched to permit oxygen injection at a plurality of locations beneath the surface of the wound.

Suitably, at least a tip region of the conduit is bioabsorbable, whereby the tip region can be left in the wound for resorption in vivo if necessary. For example, at least the tip region of the may be made from a bioabsorbable polymer such as polylactide/polyglycolide, or poly-epsilon-caprolactone.

It has been found that the conduit can function as a flow regulator for the oxygen-containing fluid under pressure, whereby the fluid is delivered to the tip of the conduit at high pressure and low flow rate. The high pressure achieves a high dissolution of oxygen and resulting high concentration of the oxygen in the physiological fluid proximate to the conduit tip. The low flow rate inhibits liquid or gas bolus formation inside the wound. In order to provide this combination of properties, at least a tip region of the conduit suitably has an effective internal diameter of less than about 75 micrometers. Preferably at least a region of the conduit has an effective internal diameter of less than about 50 micrometers, for example from about 5 to about 40 micrometers. The term "effective internal diameter" refers to the equivalent open circular internal diameter. Suitably, the said region of the conduit is located proximate to the tip (outlet) of the conduit. For example, the conduit may comprise a length of tubing having internal diameter greater than about 100 micrometers, which may be branched, the end or ends of which are joined by a suitable coupling to respective microtubes (microcatheters) having internal diameter less than about 75 micrometers for flow control, the open end or ends of the microtubes being inserted below the surface of the wound. The microtubes are suitably bioabsorbable.

It will be appreciated that considerable variation in the construction and internal geometry of the conduit is possible, provided that it delivers the oxygen-containing gas at high pressure and low flow rate.

The oxygen-containing fluid may be a liquid or a gas. The liquid is preferably aqueous, for example it may be water or a physiologically acceptable saline solution. In these embodiments the oxygen may be dissolved, preferably under pressure, to give a concentration of at least about 10 $mgO_2$ per liter, preferably at least about 20 $mgO_2$ per liter, for example from about 20 $mgO_2$ per liter to about 30 $mgO_2$ per liter. Oxygen concentrations in this range can be achieved by dissolving oxygen at a gas pressure of about 3 bar in water. The source of the fluid may be a portable pressurized reservoir containing a mixture of both fluid and oxygen bearing gas.

In other embodiments, the oxygen may be trapped in gaseous or dissolved form inside liposomes in the aqueous solution. In yet other embodiments, the liquid may be a medically acceptable perfluorocarbon solvent such as perfluorodecalin containing dissolved oxygen.

In other embodiments, the oxygen-containing fluid may be any oxygen-containing gas. Suitably, the gas comprises more than about 22 mol. % of oxygen, more suitably at least about 40 mol % oxygen, for example at least about 60 mol. % oxygen, and in some embodiments it is substantially pure oxygen. The oxygen gas may be humidified before injection into the wound. The source of gaseous oxygen may comprise a pressurized oxygen tank, which may be portable.

Suitably, the source of oxygen-enriched fluid supplies the fluid at a pressure of from about 0.1 bar to about 5 bar (gauge), more suitably from about 0.5 bar to about 2 bar, for example about 1 bar. Suitable sources comprise an infusion pump, for example a spring-driven infusion pump. Pumps of this type are described, for example, in WO-A-0038767, the entire content of which is incorporated herein by reference.

Suitably, the step of injecting the oxygen-containing fluid into the wound tissue is performed in substantially continuous fashion for a period of from about 1 hour to about 30 days, preferably from about 1 day to about 14 days.

Suitably, the pressure and delivery rate of the injection are adjusted to prevent the formation of a bolus of liquid or gas inside the wound. It will be appreciated that considerable variation in the pressure of the fluid and the internal geometry of the microcatheter is possible, provided that it results in the oxygen-containing fluid being delivered at a flow rate that is effective to promote wound healing without forming a bolus inside the wound. The effective internal diameter of the conduit, D, length of the conduit, L, the gauge pressure of the fluid used in the system, $\Delta P$, and viscosity of the fluid, $\eta$, all impact the delivery rate, V, according to the Hagen-Poiseuille equation.

$$V = \frac{\pi \Delta P D^4}{128 \eta L}$$

Typical delivery rates per wound for gaseous oxygen are suitably about 0.5 ml/hr to about 4 ml/hr, typically about 1 ml/hr to about 3 ml/hr, for example about 2 ml/hr. Typical delivery rates per wound for oxygen-enriched liquids are suitably about 0.05 ml/hr to about 1 ml/hr, typically about 0.1 ml/hr to about 0.4 ml/hr, for example about 0.15 ml/hr.

Suitably, the conduit is arranged to deliver the oxygen below any surface necrotic tissue of the wound. Suitably, the conduit is arranged to deliver the oxygen into or onto a granulation tissue in the wound. Typically, the oxygen injection is performed at a depth of from about 0.5 mm to about 10 mm below the surface of the wound, preferably from about 1 mm to about 5 mm. The invention thereby provides a good method of promoting granulation tissue beneath necrotic tissue in instances were debridement would be difficult or painful for the patient. Furthermore, by injecting at this depth it ensures that the oxygenated fluid is delivered directly to healthy tissue where it may be effective. In contrast to topical delivery, it is also more difficult for the oxygen to escape from the wound but would rather tend to remain in the tissue of the wound where it may offer therapeutic benefit to the patient.

Suitably, the wound is a chronic wound. Suitable chronic wounds include dermal ulcers such as a venous ulcers, diabetic ulcers or decubitis ulcers. The invention may also be useful for the treatment of acute wounds and burns.

It will be appreciated that any feature or combination of features that has been described above in relation to any one or more aspects of the present invention is equally useful in relation to any other of the aspects of the present invention.

An embodiment of the present invention will now be described further, by way of example, with reference to the accompanying drawings, in which:

Referring to FIG. 1, the apparatus according to the invention comprises a spring driven infusion pump 1 having a valve outlet 2. A branched extension line 3 of PTFE tubing having an internal diameter of about 1 mm has an inlet connector 4 that can be inserted in pressure-tight fashion into the pump outlet 2. The outlets at the ends of the branches of the extension line 3 are equipped with valves 5 and Luer-lock fittings for attachment with complementary fittings 7 on flow restrictor tubing 6. The flow restrictor tubing 6 is made of PVC with internal diameter about 150 micrometers. The length of the flow restrictor tubing is selected for the fluid being injected. For example, in this embodiment the length of the flow restrictor tubing is about 15 cm for liquid injection and about 40 cm for gas injection. The distal end 8 of the flow restrictor tubing 6 is joined in fluid-tight fashion to the inlet end of a microtube 9 formed of PTFE and having outside diameter about 150 micrometers, internal diameter about 49 micrometers, and length about 10 cm.

In use, according to the method of the present invention, the tip 10 of the microtube 9 is inserted into the granulation tissue of a wound, below the necrotic surface tissue of the wound and oxygen-enriched fluid is delivered through the microtube, for example under a pump pressure of about 1 bar gauge.

Figure 2:
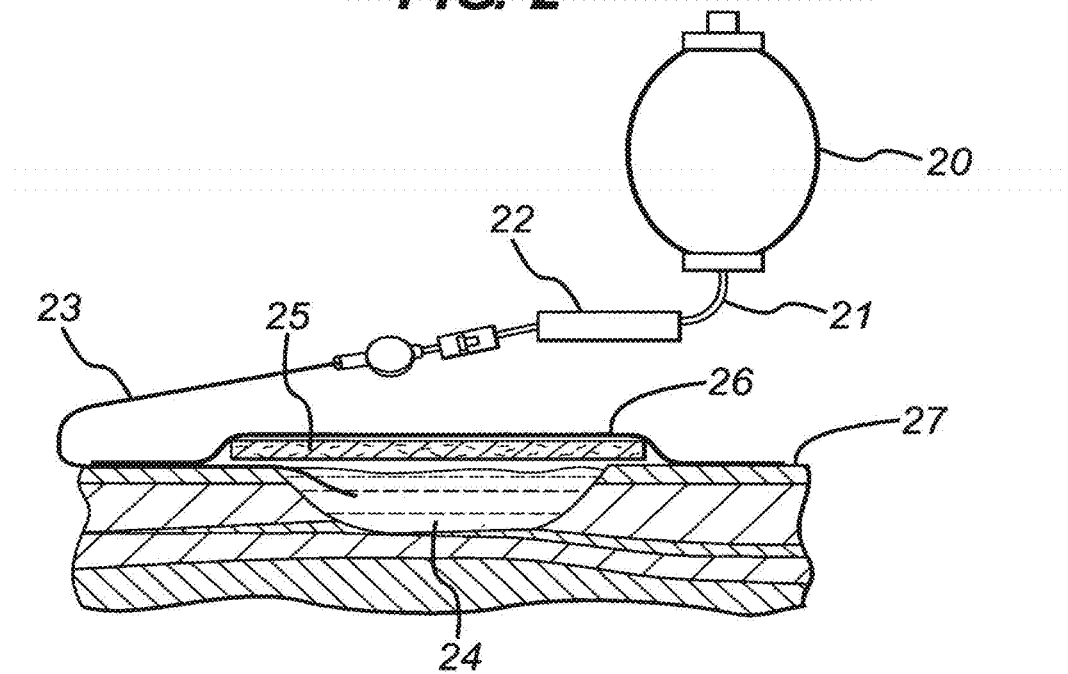
FIG. 2 shows a schematic view of a wound being treated with moist oxygen gas in accordance with the present invention.

Referring to FIG. 2, the apparatus in this embodiment is being used to inject humidified oxygen into the wound. The apparatus is generally as described in relation to FIG. 1, in particular it comprises an infusion pump 20 that delivers oxygen gas at about 1 bar gauge pressure to an extension line 21. A humidifier 22 is provided in the extension line. The humidifier comprises a moist porous material that saturates the oxygen with water vapor. The apparatus is shown injecting humidified oxygen through microtube 23 into wound 24 below the surface of the wound. The wound 24 is covered by a conventional dressing comprising an absorbent layer 25 covered by an adhesive-coated semipermeable backing layer 26 that is bonded to the skin 27 around the wound in substantially liquid-tight fashion.

Figure 3:
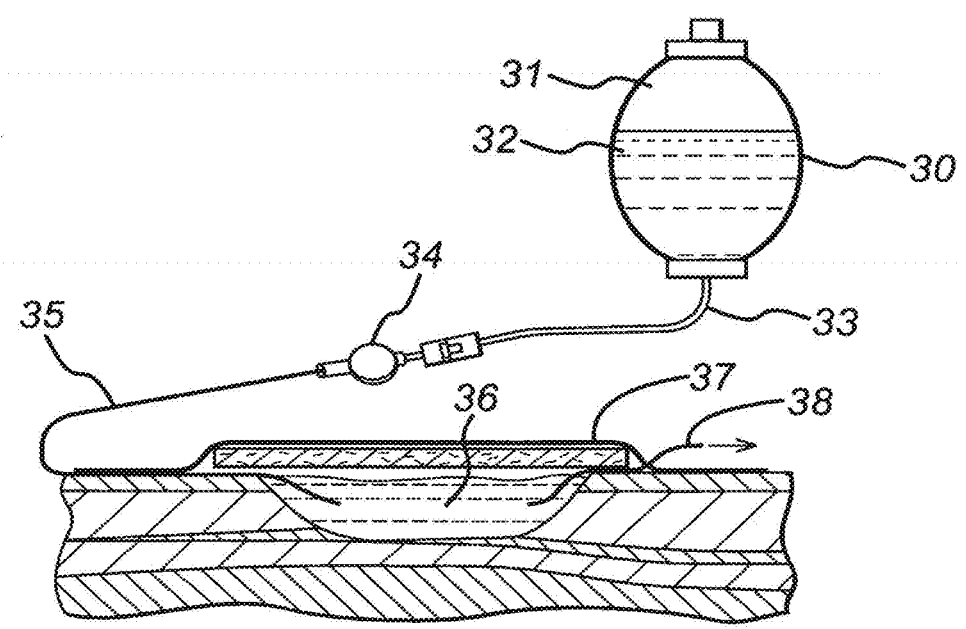
FIG. 3 shows a schematic view of a wound being treated with oxygen-enriched water in accordance with the present invention.

Referring to FIG. 3, the apparatus in this embodiment is being used to inject oxygen-enriched water into the wound. The apparatus is generally as described in relation to FIG. 1, in particular it comprises an infusion pump 30 that is filled with a mixture of oxygen gas 31 and water 32. The pump 30 delivers the water saturated with oxygen at about 1 bar gauge pressure to an extension line 33. The extension line 33 is joined by a suitable coupling 34 to microtube 35, which injects the oxygenated water into wound 36 below the surface of the wound. The wound 36 is covered by a conventional dressing 37 similar to that described in relation to FIG. 2. In addition, a drain 38 is provided to remove excess fluid from the wound.

Example 1

Standard full thickness wounds were made in a porcine model. Under anaesthesia, the back and flank skin of the pig was clipped and washed using an aseptic cleanser (Chlorhexidine −5%). The area was shaved using a razor and mopped clean using sterile swabs. Twelve full thickness wounds were created on anatomically similar sites (six on each flank). At each site a single 2.0×2.0 cm full-thickness excisional wound was created using a scalpel.

After injury, wounds were washed with sterile physiological saline and carefully swabbed dry with sterile gauze to remove any tissue debris and blood. Oxygen bearing water was delivered using microtubing as above fed into the dorsal aspect of the wound (i.e. the edge parallel to the spine) and positioned in such a way as to allow delivery to the centre of the wound. The microtubing was then fixed into position using adhesive tape (SLEEK, Registered Trade Mark of Smith & Nephew Ltd). Wounds were then dressed with 6×5 cm polyurethane foam (TIELLE, Registered Trade Mark of Johnson & Johnson) dressings in such a way as to minimise leakage. Dressings and tubing were further secured by layering topper gauze over the polyurethane foam dressings on all wounds; this was further secured with adhesive tape and Elastic netting 5 (SURGIFIX, Registered Trade Mark of Cistema d'Asti, Italy).

Wound assessment was performed on post-wounding days 2, 4 and 7. The outer surface of each dressed wound was photographed (both prior to and post cleansing). Macroscopic assessment of wound and marginal tissues was undertaken on days 2, 4 and 7. These assessments included consideration of presence and degree of inflammation, erythema, exudate, re-injury. All findings were documented and supported with photographic images.

On post wounding wound at day 7 the wound and surrounding normal tissue were excised and subsequently fixed (in 10% formalin) for routine histological assessment. Tissue slices were embedded in paraffin wax, sectioned (71 μm) and representative sections stained with Haematoxylin and Eosin (H&E). Image analysis based quantitative assessment of wound width (contraction), granulation tissue deposition (granulation tissue depth and granulation tissue area) was then performed.

Oxygen enriched water was delivered to the microcatheter at about 1 bar gauge. The resulting oxygen-enriched water is estimated to contain 25-30 mg/l of oxygen. Five wounds were treated as reference examples, and received purely topical delivery (i.e. the microcatheter remained on top of the newly formed tissue). In one wound the microcatheter was embedded in the newly formed tissue (wound 19.2.10 in Table 1) resulting in oxygen being delivered from inside the wound. During treatment, an island-type adhesive dressing comprising a sheet of hydrophilic polyurethane foam (TIELLE®, available from Johnson & Johnson Medical) was applied over the wounds.

Figure 4A:
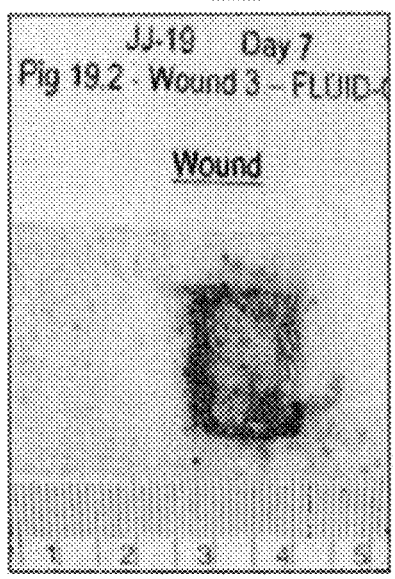
FIG. 4A shows a photograph of a wound following delivery of oxygen-enriched water for 7 days topically onto the surface of the wound as described for the reference examples in Example 1.
Figure 4B:
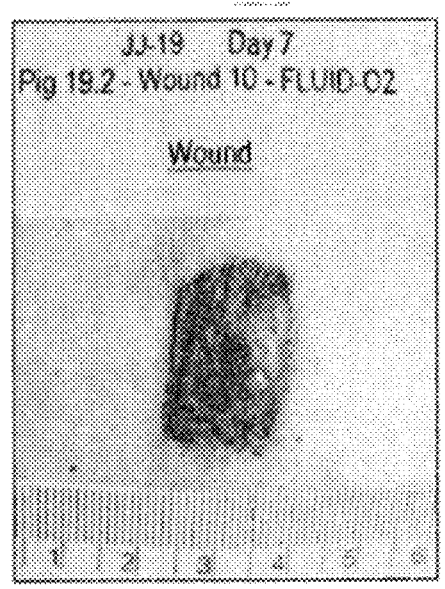
FIG. 4B shows a photograph of a wound following delivery of oxygen-enriched water for 7 days injected below the tissue surface of the wound as described in accordance with the invention in Example 1.

The appearance of the wounds following delivery of oxygen for 7 days is shown in FIGS. 4A and 4B, wherein it can be seen that the extent of new tissue formation was higher in the wound that received oxygen-enriched water injected below the tissue surface (Wound 10 in FIG. 4B) in comparison to a wound that received oxygen-enriched water topically (Wound 3 in FIG. 4A). The differences are striking. It is unusual in an in vivo model to see such large differences by eye.

The results were confirmed by histological determination of the amount of granulation tissue. The results are shown in Table 1.

TABLE 1

| Animal | Granulation Mean depth (mm) | Granulation Tissue Area (mm$^2$) | Total granulation Volume (mm$^3$) |
|---|---|---|---|
| 19.02.01 | 4.01 | 63.38 | 254 |
| 19.01.03 | 4.57 | 82.95 | 379 |
| 19.02.05 | 7.28 | 102.72 | 748 |
| 19.02.08 | 4.39 | 81.04 | 599 |
| 19.02.10 | 6.52 | 128.66 | 839 |
| 19.02.12 | 6.12 | 101.50 | 621 |

Only animal 19.02.10 had oxygen-enriched water delivered into tissue. All others had the fluid delivered from above. These results show that the total granulation deposition volume (depth×area) was 839 mm$^3$ for the wound to which oxygen was delivered into the tissue compared to an average granulation volume of 520.2±199 mm$^3$ for the wound to which oxygen-enriched water was delivered onto (not into) the tissue.

The above embodiment has been described by way of example only. Many other embodiments falling within the scope of the accompanying claims will be apparent to the skilled reader.

The invention claimed is:

1. A method of treatment of a wound, said method comprising the step of injecting an effective amount of an oxygen-containing fluid selectively and directly into a layer of wound tissue located below a surface layer of said wound, said step of injecting being carried out through a conduit having one or more outlets for said fluid, wherein all of said outlets are positioned below the surface of the wound during said step of injecting, and wherein pressure and delivery rate of the injection are adjusted to prevent the formation of a bolus of liquid or gas inside the wound.

2. The method of claim 1, wherein the oxygen-containing fluid is a liquid containing dissolved oxygen.

3. The method of claim 2, wherein the liquid is water and the oxygen is dissolved therein in an amount greater than about 10 mg per liter.

4. The method of claim 1, wherein the oxygen-containing fluid is an oxygen-containing gas.

5. The method of claim 4, wherein the partial pressure of oxygen in said gas is greater than about 0.25 bar.

6. The method of claim 1, wherein the step of injecting is performed in continuous fashion for a period of from about 1 hour to about 30 days.

7. A method of treatment of a wound according to claim 1, wherein the conduit is configured to deliver the oxygen-containing fluid below a surface necrotic tissue layer of the wound.

8. A method of treatment of a wound according to claim 1, wherein the conduit is configured to deliver the oxygen into or onto a granulation tissue in the wound.

9. A method of treatment of a wound according to claim 1, wherein the wound is a chronic wound.

10. A method of treatment of a wound according to claim 1, wherein the conduit is formed from a microcatheter or a syringe.

11. A method of treatment of a wound according to claim 1, wherein at least a part of the conduit is bioabsorbabale.

12. A method of treatment of a wound according to claim 1, wherein the method does not comprise damage to tissue surrounding the wound.

13. A method of treatment of a wound according to claim 1, wherein the conduit has an effective lumen diameter of less than about 75 micrometers.

14. A method of treatment of a wound according to claim 1, wherein the oxygen containing fluid is supplied to the conduit at elevated pressure.

15. The method of claim 1 wherein the step of injecting is performed in continuous fashion for a period of from about 1 day to about 14 days.

16. A method of treatment of a wound according to claim 1, wherein the method does not comprise damage to tissue surrounding the wound by suturing.

17. A Method of treatment of a wound, said method comprising the step of injecting an effective amount of an oxygen-containing fluid selectively and directly into a layer of wound tissue located below a surface layer of said wound, said step of injecting being carried out through a conduit having one or more outlets for said fluid, wherein all of said outlets are positioned below the surface of the wound during said step of injecting, and wherein the conduit is configured to deliver the oxygen-containing fluid below a surface necrotic tissue layer of the wound.

* * * * *